US00PP34838P2

(12) United States Plant Patent
Uebelhart

(10) Patent No.: US PP34,838 P2
(45) Date of Patent: Dec. 13, 2022

(54) ***GYPSOPHILA* PLANT NAMED 'JEGYPCEPLE'**

(50) Latin Name: *Acanthophyllum cerastioides*
Varietal Denomination: JEGYPCEPLE

(71) Applicant: JELITTO STAUDENSAMEN GmbH, Schwarmstedt (DE)

(72) Inventor: Georg Uebelhart, Salzhausen (DE)

(73) Assignee: JELITTO STAUDENSAMEN GmbH, Schwarmstedt (DE)

( * ) Notice: Subject to any disclaimer, the term of this patent is extended or adjusted under 35 U.S.C. 154(b) by 0 days.

(21) Appl. No.: 17/859,385

(22) Filed: Jul. 7, 2022

(51) Int. Cl.
*A01H 5/02* (2018.01)
*A01H 6/30* (2018.01)

(52) U.S. Cl.
USPC ..... Plt./354

(58) Field of Classification Search
USPC ..... Plt./354
See application file for complete search history.

*Primary Examiner* — Annette H Para
(74) *Attorney, Agent, or Firm* — C. Anne Whealy

(57) ABSTRACT

A new and distinct cultivar of *Gypsophila* plant named 'JEGYPCEPLE', characterized by its compact and broadly spreading to prostrate plant habit; moderately vigorous to vigorous growth habit; freely branching habit; dense and bushy habit; large double type white-colored flowers with reddish purple-colored venation; relatively long flowering period; good garden performance and winter hardiness.

3 Drawing Sheets

Figure 1:
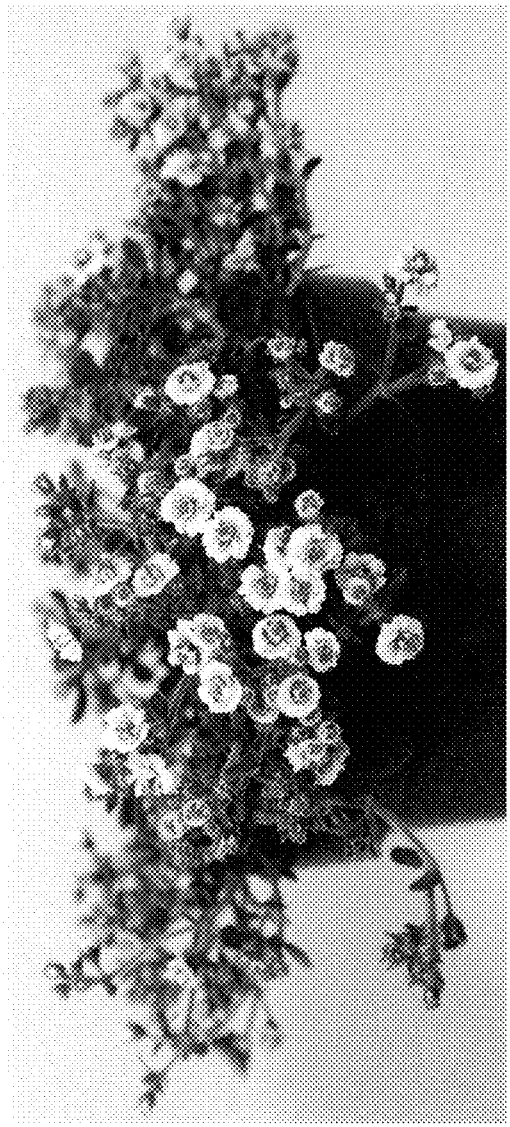

Botanical designation: *Acanthophyllum cerastioides.*
Cultivar denomination: 'JEGYPCEPLE'.

STATEMENT REGARDING PRIOR DISCLOSURES BY INVENTOR & APPLICANT/ASSIGNEE

An European Plant Breeder's Rights application for the instant plant was filed by the Applicant, Jelitto Staudensamen GmbH of Schwarmstedt, Germany on Oct. 13, 2021, application number 2021/2566. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Gypsophila* plant, botanically known as *Acanthophyllum cerastioides* (syn. *Gypsophila cerastioides*), grown commercially as a potted plant, and hereinafter referred to by the name 'JEGYPCEPLE'.

The new *Gypsophila* plant is a product of a planned breeding program conducted by the Inventor in Schwarmstedt, Germany. The objective of the breeding program is to create new compact and uniform *Gypsophila* plants with numerous double flowers.

The new *Gypsophila* plant originated from an open-pollination conducted by the Inventor in Schwarmstedt, Germany in 2013 of a proprietary selection of *Acanthophyllum cerastioides* identified as code number G12051, not patented, as the female, or seed, parent with an unknown selection of *Acanthophyllum cerastioides* as the male, or pollen, parent. The new *Gypsophila* plant was discovered and selected by the Inventor as a single flowering plant from within the progeny of the stated open-pollination in a controlled environment in Schwarmstedt, Germany in 2015.

Asexual reproduction of the new *Gypsophila* plant by terminal cuttings in a controlled environment in Hendrik-Ido-Ambacht, The Netherlands since 2016 has shown that the unique features of this new *Gypsophila* plant are stable and reproduced true to type in successive generations.

SUMMARY OF THE INVENTION

Plants of the new *Gypsophila* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'JEGYPCEPLE'. These characteristics in combination distinguish 'JEGYPCEPLE' as a new and distinct *Gypsophila* plant:

1. Compact and broadly spreading to prostrate plant habit.
2. Moderately vigorous to vigorous growth habit.
3. Freely branching habit; dense and bushy habit.
4. Large double type white-colored flowers with reddish purple-colored venation.
5. Relatively long flowering period.
6. Good garden performance and winter hardiness.

In side-by-side comparisons, plants of the new *Gypsophila* differed primarily from plants of the female parent selection in flower form as plants of the new *Gypsophila* have double type flowers whereas plants of the female parent selection have single type flowers.

Plants of the new *Gypsophila* can also be compared to plants of *Acanthophyllum cerastioides* 'Pixie Splash', not patented. In side-by-side comparisons, plants of the new *Gypsophila* differ from plants of 'Pixie Splash' in the following characteristics:

1. Plants of the new *Gypsophila* are more compact than plants of 'Pixie Splash'.
2. Plants of the new *Gypsophila* have larger flowers than plants of 'Pixie Splash'.
3. Plants of the new *Gypsophila* have double type flowers whereas plants of 'Pixie Splash' have single type flowers.
4. Plants of the new *Gypsophila* flower for about eight weeks whereas plants of 'Pixie Splash' flower for about four weeks.

BRIEF DESCRIPTION OF THE PHOTOGRAPHS

The accompanying photographs illustrate the overall appearance of the new *Gypsophila* plant showing the colors as true as it is reasonably possible to obtain in colored reproductions of this type. Colors in the photograph may differ slightly from the color values cited in the detailed botanical description which accurately describe the colors of the new *Gypsophila* plant.

The photograph on the first sheet (FIG. 1) is a side perspective view of a typical flowering plant of 'JEGYPCEPLE' grown in a container.

Figure 2:
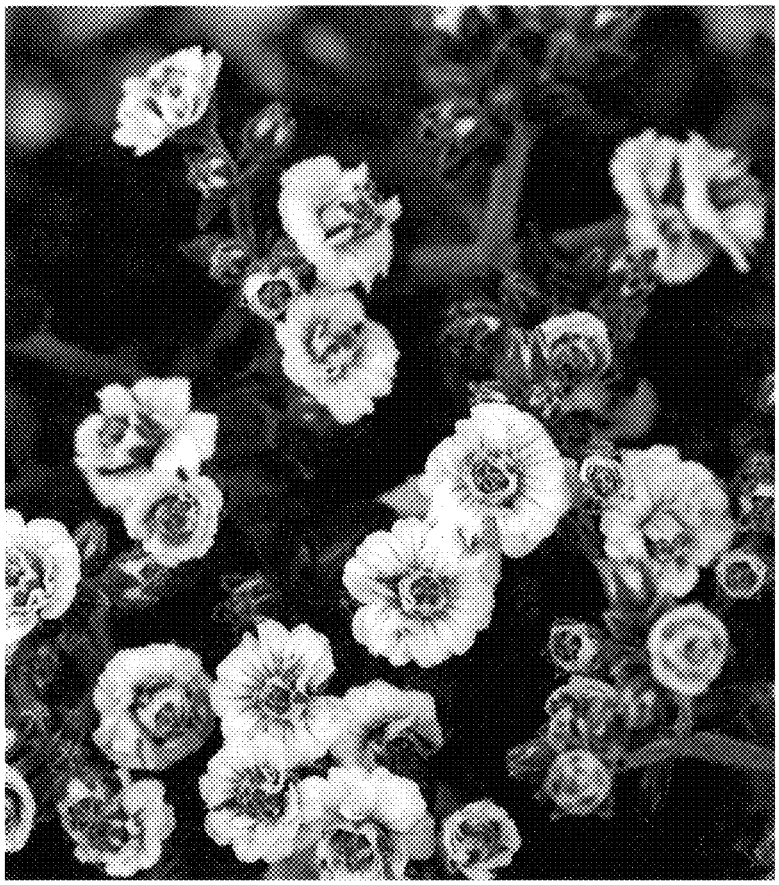

The photograph on the second sheet (FIG. 2) is a close-up view of a typical flowering plant of 'JEGYPCEPLE'.

Figure 3:
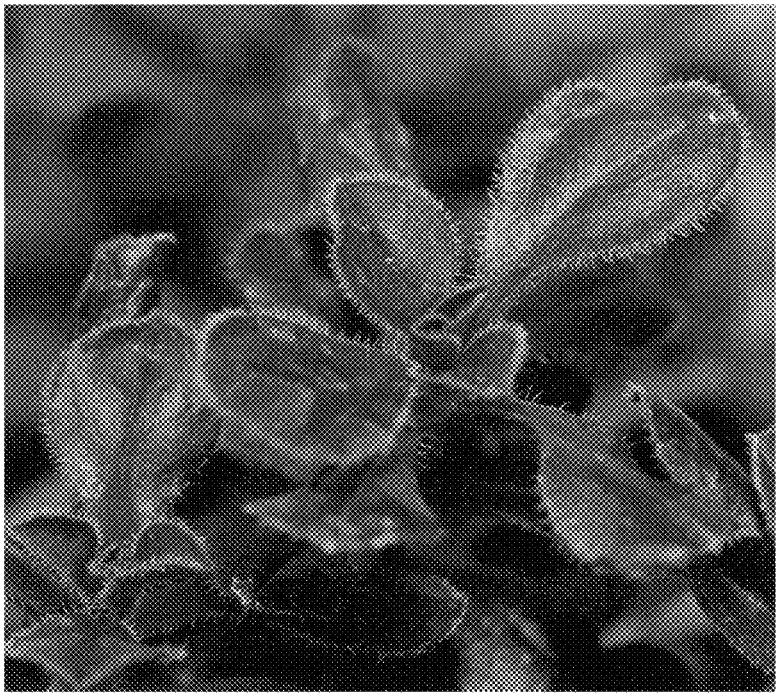

The photograph on the third sheet (FIG. 3) is a close-up view of typical leaves of 'JEGYPCEPLE'.

DETAILED BOTANICAL DESCRIPTION

The aforementioned photographs and following observations and measurements describe plants grown during the late winter and early spring in 12-cm containers in a glass-covered greenhouse in Hendrik-Ido-Ambacht, The Netherlands and under cultural practices which approximate those generally used in commercial potted *Gypsophila* production. During the production of the plants, day temperatures ranged from 6.6° C. to 14° C. and night temperatures ranged from 3.7° C. to 11.9° C. Flowering plants were seven months old when the photographs and the detailed description were taken. In the following description, color references are made to The Royal Horticultural Society Colour Chart, Fourth Edition, 2015, except where general terms of ordinary dictionary significance are used.

Botanical classification: *Acanthophyllum cerastioides* 'JEGYPCEPLE'.

Parentage:

*Female, or seed, parent.*—Proprietary selection of *Acanthophyllum cerastioides* identified as code number G12051, not patented.

*Male, or pollen, parent.*—Unknown selection of *Acanthophyllum cerastioides*, not patented.

Propagation:

*Type.*—By terminal cuttings.

*Time to initiate roots, summer and winter.*—About two weeks at temperatures about 20° C.

*Time to produce a rooted young plant, summer.*—About four weeks at temperatures about 20° C.

*Time to produce a rooted young plant, winter.*—About five weeks at temperatures about 20° C.

*Root description.*—Medium in thickness, fibrous; typically white in color, actual color of the roots is dependent on substrate composition, water quality, fertilizers, substrate temperature and physiological age of roots.

*Rooting habit.*—Freely branching, medium density.

Plant description:

*Appearance.*—Herbaceous perennial potted plant; compact and broadly spreading to prostrate plant habit; moderately vigorous to vigorous growth habit and moderate growth rate.

*Branching habit.*—Freely branching habit; dense and bushy habit; about eight primary lateral branches each with about eight secondary lateral branches; pinching will enhance branching potential.

*Plant height, soil level to top of foliar plane.*—About 7 cm.

*Plant height, soil level to top of floral plane.*—About 7.1 cm.

*Plant diameter or spread.*—About 22 cm.

*Lateral branches.*—Length: About 6 cm. Diameter: About 1.2 mm. Internode length: About 1.1 cm. Strength: Moderately strong. Aspect: About 80° from vertical. Texture and luster: Densely pubescent; moderately glossy. Color, developed: Close to 146B to 146C. Color, developed: Upper surface, close to N148A to N148B tinged with close to 197A; lower surface, close to 146C.

Leaf description:

*Arrangement.*—Opposite, simple.

*Length.*—About 1 cm.

*Width.*—About 7.5 mm.

*Shape.*—Broadly obovate to obovate.

*Apex.*—Rounded to shallowly retuse.

*Base.*—Attenuate.

*Margin.*—Entire; coarsely undulate.

*Texture and luster, upper surface.*—Smooth, glabrous except for margins which are moderately pubescent; slightly glossy.

*Texture and luster, lower surface.*—Smooth, glabrous except for margins which are moderately pubescent; moderately glossy.

*Venation pattern.*—Parallel.

*Color.*—Developing leaves, upper surface: Close to 137A. Developing leaves, lower surface: Close to 143A to 143B. Fully expanded leaves, upper surface: Close to NN137A to NN137B; venation, close to 137A. Fully expanded leaves, lower surface: Close to 146B; venation, close to 146B to 146C.

*Petioles.*—Length: About 4 mm. Diameter: About 1.2 mm by 2 mm. Strength: Strong. Texture and luster, upper and lower surfaces: Smooth, glabrous except for margins which are moderately pubescent; slightly glossy. Color, upper and lower surfaces: Close to 144B.

Flower description:

*Flower arrangement and habit.*—Terminal compound cymes with white-colored flowers, flowers rotate and fully double; freely flowering habit, about 30 flowers per inflorescence and about 1,900 flowers developing per plant during the flowering season; flowers face outwardly to upright.

*Flowering response.*—In The Netherlands, plants of the new *Gypsophila* flower from late spring into the autumn; plants begin flowering about seven months after planting.

*Post-production longevity.*—Individual flowers last about one week on the plant; flowers not persistent.

*Fragrance.*—None detected.

*Inflorescence height.*—About 3.5 cm.

*Inflorescence diameter.*—About 4.2 cm.

*Flower diameter.*—About 1.2 cm.

*Flower depth* (*height*).—About 9 mm.

*Flower buds.*—Length: About 3 mm. Diameter: About 2 mm. Shape: Broadly ovate. Texture and luster: Densely pubescent; matte. Color: Close to 138B to 138C; distally, close to 137B; immature petals, close to 155B.

*Petals.*—Quantity per flower and arrangement: About five in a single whorl. Length: About 5 mm. Width: About 4.5 mm. Shape: Broadly obovate to close to flabellate; slightly to moderately reflexed. Apex: Rounded, irregular. Base: Attenuate. Margin: Entire. Texture and luster, upper surface: Smooth, glabrous; slightly glossy. Texture and luster, lower surface: Smooth, glabrous; matte to slightly glossy. Color: When opening, upper surface: Close to NN155C to NN155D; venation, tinged with close to 182C. When opening, lower surface: Close to NN155C; venation, tinged with close to 182B to 182C. Fully opened, upper surface: Close to NN155D; venation, close to 64A; color does not change with subsequent development. Fully opened, lower surface: Close to NN155D; venation, close to 61A; color does not change with subsequent development.

*Petaloids* (*transformed reproductive structures*).—Quantity per flower and arrangement: About 20 in about four whorls interior to the petals. Length: About 6 mm. Width: About 3.5 mm. Shape: Obovate to narrowly obovate. Apex: Rounded, irregular. Base: Attenuate. Margin: Entire; slightly undulate. Texture and luster, upper surface: Smooth, glabrous; slightly glossy. Texture and luster, lower surface: Smooth, glabrous; matte to slightly glossy. Color: When opening, upper surface: Close to NN155C to NN155D; venation, tinged with close to 182C. When opening, lower surface: Close to NN155C; venation, tinged with close to 182B to 182C. Fully opened, upper surface: Close to NN155D; venation, close to 64A; color does not change with subsequent development. Fully opened, lower surface: Close to NN155D; venation, close to 61A; color does not change with subsequent development.

*Sepals.*—Quantity per flower and arrangement: About five in a single whorl; lower 50% of the sepals are fused. Length: About 5 mm. Width: About 1.5 mm. Shape: Narrowly ovate. Apex: Narrowly acute. Margin: Entire. Texture and luster, upper surface: Smooth, glabrous with exception of margins which are moderately pubescent; slightly glossy. Texture and luster, lower surface: Densely pubescent; matte. Color: When developing, upper surface: Close to 144B; venation, close to 143B. When developing, lower surface: Close to 144B; towards the apex, close to 144A. Fully developed, upper surface: Close to 144A; venation, close to 143B. Fully developed, lower surface: Close to 144A.

*Peduncles.*—Length: About 1.8 cm. Diameter: About 1.2 mm. Aspect: About 35° from the stein axis. Strength: Strong. Texture and luster: Densely pubescent; slightly glossy. Color: Close to 144A.

*Pedicels.*—Length: About 7 mm. Diameter: About 0.8 mm. Aspect: About 0° to 35° from peduncle axis. Strength: Moderately strong. Texture and luster: Densely pubescent; slightly glossy. Color: Close to 144A.

*Reproductive organs.*—To date, stamen and pistil development have not been observed on plants of the new *Gypsophila*.

*Seeds and fruits.*—To date, seed and fruit production has not been observed on plants of the new *Gypsophila*.

Pathogens & pest resistance: Plants of the new *Gypsophila* have not been observed to be resistant to pathogens and pests and pests common to *Gypsophila* plants.

Garden performance: Plants of the new *Gypsophila* have been observed to have good garden performance and to tolerate temperatures ranging from about −28° C. to about 40° C. and to be suitable for USDA Hardiness Zones 5 through 10.

It is claimed:

1. A new and distinct *Gypsophila* plant named 'JEGYPCEPLE' as illustrated and described.

* * * * *